United States Patent
Lee et al.

(10) Patent No.: US 10,006,926 B2
(45) Date of Patent: Jun. 26, 2018

(54) SPECIMEN INSPECTION APPARATUS

(71) Applicant: SAMSUNG ELECTRONICS CO., LTD., Suwon-si (KR)

(72) Inventors: Young-goun Lee, Seoul (KR); Jung-ki Min, Yongin-si (KR); Jong-gun Lee, Yongin-si (KR); Hyun-ju Jung, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 83 days.

(21) Appl. No.: 14/876,171

(22) Filed: Oct. 6, 2015

(65) Prior Publication Data
US 2016/0282372 A1     Sep. 29, 2016

(30) Foreign Application Priority Data
Mar. 24, 2015  (KR) ........................ 10-2015-0040959

(51) Int. Cl.
*G01N 35/00* (2006.01)
*B01L 3/00* (2006.01)

(52) U.S. Cl.
CPC .. *G01N 35/00069* (2013.01); *B01L 3/502715* (2013.01); *B01L 2200/023* (2013.01); *B01L 2200/027* (2013.01); *B01L 2300/0851* (2013.01); *B01L 2300/0864* (2013.01); *B01L 2400/0409* (2013.01)

(58) Field of Classification Search
CPC .............................................. G01N 35/00069
See application file for complete search history.

(56) References Cited

U.S. PATENT DOCUMENTS 8,609,038 B2 * 12/2013 Kim .................. B01L 3/502715
                                                     422/50
8,623,296 B2    1/2014 Desmond et al.
8,685,340 B2    4/2014 Hasan et al.
(Continued)

FOREIGN PATENT DOCUMENTS

EP        2073018 A1    6/2009
EP        2416163 A1    2/2012
(Continued)

OTHER PUBLICATIONS

International Search Report and Written Opinion, dated Jan. 25, 2016 by International Searching Authority in counterpart International Application No. PCT/KR2015/010966. (PCT/ISA/220, PCT/ISA/210 & PCT/ISA/237).
(Continued)

*Primary Examiner* — Clayton E Laballe
*Assistant Examiner* — Dennis Hancock
(74) *Attorney, Agent, or Firm* — Sughrue Mion, PLLC

(57) ABSTRACT

A specimen inspection apparatus into which a specimen transporting apparatus is inserted, the specimen inspection apparatus including: a platform including an upper plate and a lower plate disposed to face each other and to be spaced apart from each other by a predetermined distance; an injection part provided in the upper plate, a front end of the specimen transporting apparatus being inserted into the injection part; an introduction part connected to the injection part and provided between the upper and lower plate; and a plurality of stepped parts provided in the introduction part.

15 Claims, 13 Drawing Sheets

(56) References Cited

U.S. PATENT DOCUMENTS

| | | | |
|---|---|---|---|
| 9,527,079 B2* | 12/2016 | Park | ............... B01L 3/502715 |
| 2004/0232074 A1 | 11/2004 | Peters et al. | |
| 2005/0176059 A1* | 8/2005 | Pal | ................... B01L 3/0275 |
| | | | 435/7.1 |
| 2010/0050751 A1 | 3/2010 | Lee | |
| 2012/0024083 A1* | 2/2012 | Wo | ................ B01L 3/502738 |
| | | | 73/863.21 |
| 2012/0190032 A1* | 7/2012 | Ness | ............. B01L 3/502715 |
| | | | 435/6.12 |
| 2014/0004527 A1* | 1/2014 | Oka | ................ G01N 15/1484 |
| | | | 435/6.15 |
| 2016/0038939 A1 | 2/2016 | Min et al. | |

FOREIGN PATENT DOCUMENTS

| | | |
|---|---|---|
| WO | 2012/160923 A1 | 11/2012 |
| WO | 2014/078100 A1 | 5/2014 |

OTHER PUBLICATIONS

Communication dated Jan. 19, 2018, issued by the European Patent Office in counterpart European Application No. 15886585.7.

* cited by examiner

SPECIMEN INSPECTION APPARATUS

CROSS-REFERENCE TO RELATED APPLICATION

This application claims priority from Korean Patent Application No. 10-2015-0040959, filed on Mar. 24, 2015 in the Korean Intellectual Property Office, the disclosure of which is incorporated herein by reference in its entirety.

BACKGROUND

1. Field

Apparatuses and methods consistent with exemplary embodiments relate to specimen inspection apparatuses.

2. Description of the Related Art

Specimen inspection apparatuses, for example, pipette apparatuses, are widely used in fields (e.g., molecular biology) in which a comparatively small amount of liquid (for example, an amount covering in a micrometer range) is measured. The pipette apparatuses may be in the form of pipette robots each having an individual pipette unit or in the form of a plurality of individual pipette units that operate simultaneously or individually, or in the form of manual pipette apparatuses or pipette machines.

A front end of a specimen transporting apparatus, for example, a pipette tip, may be an elongated type sleeve for measuring a small amount of liquid, which has a central penetration opening that extends along a longitudinal axis and tapers off in a substantially conical shape. For example, an end (coupling end) of the pipette tip having a large width slides onto an injection part of a pipette apparatus, and a sharp end that faces the end having the large width in an axial direction, is immersed in a medium to be pipetted. In the related art, the pipette tip is constructed to be used once. That is, the pipette tip may be used once and then may be discarded.

In order to ensure precise measurement, an apparatus for transporting a small amount of a specimen, such as the pipette tip, has to be safely and solidly connected to a specimen inspection apparatus. This feature is required, in particular, when safe insertion and precise positioning of the individual specimen transporting apparatus cannot be manually checked. Also, manufacturing of the specimen inspection apparatus has to be performed in such a way that the specimen inspection apparatus offers simple maintenance and increased cost efficiency.

SUMMARY

One or more exemplary embodiments provide specimen inspection apparatuses in which specimen transporting apparatuses having front ends of various sizes may be used.

Additional aspects will be set forth in part in the description which follows and, in part, will be apparent from the description, or may be learned by practice of the presented exemplary embodiments.

According to an aspect of an exemplary embodiment, there is provided a specimen inspection apparatus into which a specimen transporting apparatus is inserted, including: a platform including an upper plate and a lower plate disposed to face each other and to be spaced apart from each other by a predetermined distance; an injection part, which is disposed in the upper plate and into which a front end of the specimen transporting apparatus is inserted; an introduction part, which is connected to the injection part and into which a specimen is introduced; and a plurality of stepped parts disposed in the introduction part.

A diameter of the injection part may be larger than a diameter of the front end.

The front end may include an opening through which the specimen is injected, and each of the plurality of stepped parts may include support surfaces disposed to face the injection part, and a width of each of the support surfaces may be smaller than a diameter of the opening.

A width of each support surface may be equal to or less than a half of the diameter of the opening.

The specimen inspection apparatus may further include one or more projection parts formed on the support surfaces and disposed to face the injection part.

A length of each of the one or more projection parts may be larger than the diameter of the opening disposed in the front end, and a width of each projection part may be smaller than the diameter of the opening disposed in the front end.

When the plurality of projection parts are disposed on the support surfaces to be spaced apart from each other by a predetermined distance, the predetermined distance may be smaller than a diameter of the front end.

The specimen inspection apparatus may further include one or more groove parts formed in the support surfaces and disposed to face the injection part.

A width of each of the one or more groove parts may be smaller than a diameter of the front end of the specimen transporting apparatus.

When the plurality of groove parts are disposed on the support surfaces to be spaced apart from each other by a predetermined distance, a length of each groove part may be larger than the diameter of the opening disposed in the front end, and the predetermined distance may be smaller than a diameter of the opening disposed in the front end.

The specimen inspection apparatus may further include one or more projection parts formed on the lower plate and disposed to face the injection part.

The specimen inspection apparatus may further include a side part forming a predetermined angle with the lower plate and disposed between the stepped part and the lower plate.

The front end may include an opening through which the specimen is injected, and a length of each projection part may be larger than the diameter of the opening disposed in the front end, and a width of each projection part may be smaller than the diameter of the opening disposed in the front end.

When the plurality of projection parts are disposed on the lower plate to be spaced apart from each other by a predetermined distance, the predetermined distance may be smaller than the diameter of the front end.

The specimen inspection apparatus may further include one or more groove parts formed in the lower plate and disposed to face the injection part.

A width of each of the one or more groove parts may be smaller than a diameter of the front end of the specimen transporting apparatus.

When the plurality of groove parts are disposed in the lower plate to be spaced apart from each other by a predetermined distance, the front end may include an opening through which the specimen is injected, a length of each groove part may be larger than the diameter of the opening disposed in the front end, and the predetermined distance may be smaller than the diameter of the opening disposed in the front end.

The specimen transporting apparatus may be a pipette.

According to an aspect of an exemplary embodiment, there is provided a specimen inspection apparatus into which a specimen transporting apparatus is inserted, including: a platform comprising an upper plate and a lower plate disposed to face each other and to be spaced apart from each other by a predetermined distance; an injection part provided in the upper plate, a front end of the specimen transporting apparatus being inserted into the injection part; an introduction part connected to the injection part and provided between the upper and lower plate; and a plurality of stepped parts provided in the introduction part.

A diameter of the injection part may be larger than a diameter of the front end of the specimen transporting apparatus.

The front end may include an opening through which specimen is injected into or ejected out of the specimen transporting apparatus, and the plurality of stepped parts may include a first step part including a first support surface and a second step part including a second support surface, the first and second support surfaces disposed to face the injection part, and a width of each of the first and second support surfaces is smaller than a diameter of the opening of the specimen transporting apparatus.

The width of each of the first and second support surfaces is less than or equal to a half of the diameter of the opening.

The specimen inspection apparatus may further include a projection part provided on each of the first and second support surfaces and facing the injection part.

A length of the projection part may be larger than the diameter of the opening disposed in the front end, and a width of the projection part is smaller than the diameter of the opening disposed in the front end.

The projection part may include a plurality of projection parts, the plurality of projection parts provided on each of the first and second support surfaces and provided to be spaced apart from one another by a predetermined distance, the predetermined distance being smaller than a diameter of the front end.

The specimen inspection apparatus may further include a groove part provided in each of the first and second support surfaces and facing the injection part.

A width of the groove part may be smaller than a diameter of the front end of the specimen transporting apparatus.

The groove part may include a plurality of groove parts, the plurality of groove parts are provided on each of the first and second support surfaces and provided to be spaced apart from one another by a predetermined distance, and a length of each groove part may be larger than the diameter of the opening disposed in the front end, and the predetermined distance is smaller than the diameter of the opening disposed in the front end.

The specimen inspection apparatus may further include a projection part provided on the lower plate and facing the injection part.

The specimen inspection apparatus may further include a side part forming a predetermined angle with the lower plate and provided between the stepped part and the lower plate.

The front end may include an opening through which specimen is injected into or ejected out of the specimen transporting apparatus, and wherein a length of the projection part is larger than the diameter of the opening disposed in the front end, and a width of the projection part is smaller than the diameter of the opening disposed in the front end.

The projection part may include a plurality of projection parts, the plurality of projection parts provided on the lower plate and spaced apart from one another by a predetermined distance, the predetermined distance being smaller than the diameter of the front end.

The specimen inspection apparatus may further include a groove part provided in the lower plate and facing the injection part.

A width of the groove part may be smaller than a diameter of the front end of the specimen transporting apparatus.

The groove part may include a plurality of groove parts, the plurality of groove parts provided in the lower plate and spaced apart from one another by a predetermined distance, wherein the front end comprises an opening through which specimen is injected into or ejected out of the specimen transporting apparatus, a length of each groove part being larger than the diameter of the opening disposed in the front end, and the predetermined distance being smaller than the diameter of the opening disposed in the front end.

The plurality of stepped parts may include a first step part including a first support surface and a second step part including a second support surface, and wherein a length of each of the first and second support surfaces is smaller than a diameter of the front end of the specimen transporting apparatus.

BRIEF DESCRIPTION OF THE DRAWINGS

The above and/or other aspects of the disclosure will become apparent and more readily appreciated from the following description of the exemplary embodiments, taken in conjunction with the accompanying drawings in which.

DETAILED DESCRIPTION

Figure 1:
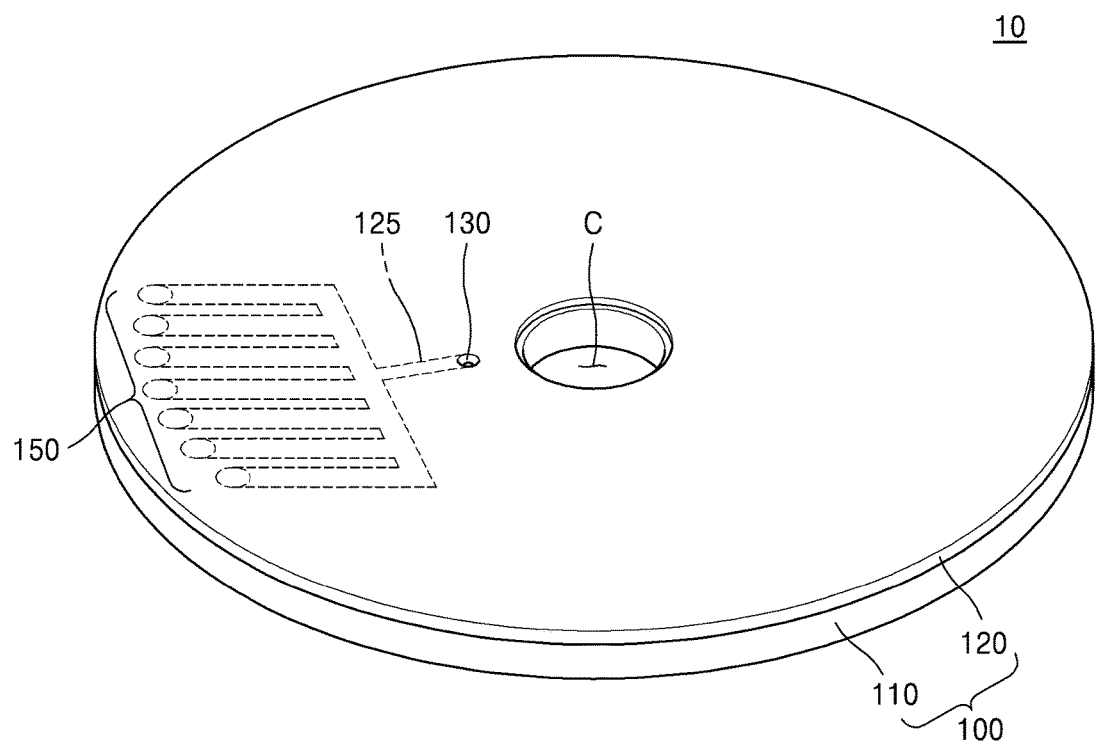
FIG. 1 is a perspective view of a specimen inspection apparatus according to an exemplary embodiment.

Reference will now be made in detail to exemplary embodiments, examples of which are illustrated in the accompanying drawings, wherein like reference numerals refer to like elements throughout. In this regard, the exemplary embodiments may have different forms and should not be construed as being limited to the descriptions set forth herein. Accordingly, the exemplary embodiments are merely described below, by referring to the figures, to explain aspects of the inventive concept.

Terms used herein will be briefly described, and exemplary embodiments will be described in detail.

General terms that are currently and widely used in consideration of functions of the terms in exemplary embodiments are selected as terms used in exemplary embodiments. However, these terms may differ according to an intention or a practice of one of ordinary skill in the art, or emergence of new technology. Also, in a particular case, the applicant may arbitrarily select terms. In such a case, the meaning of the terms will be described in detail in the description of the inventive concept. Thus, the terms used in exemplary embodiments are not simply names but should be defined based on their meaning and the exemplary embodiments.

Figure 2:
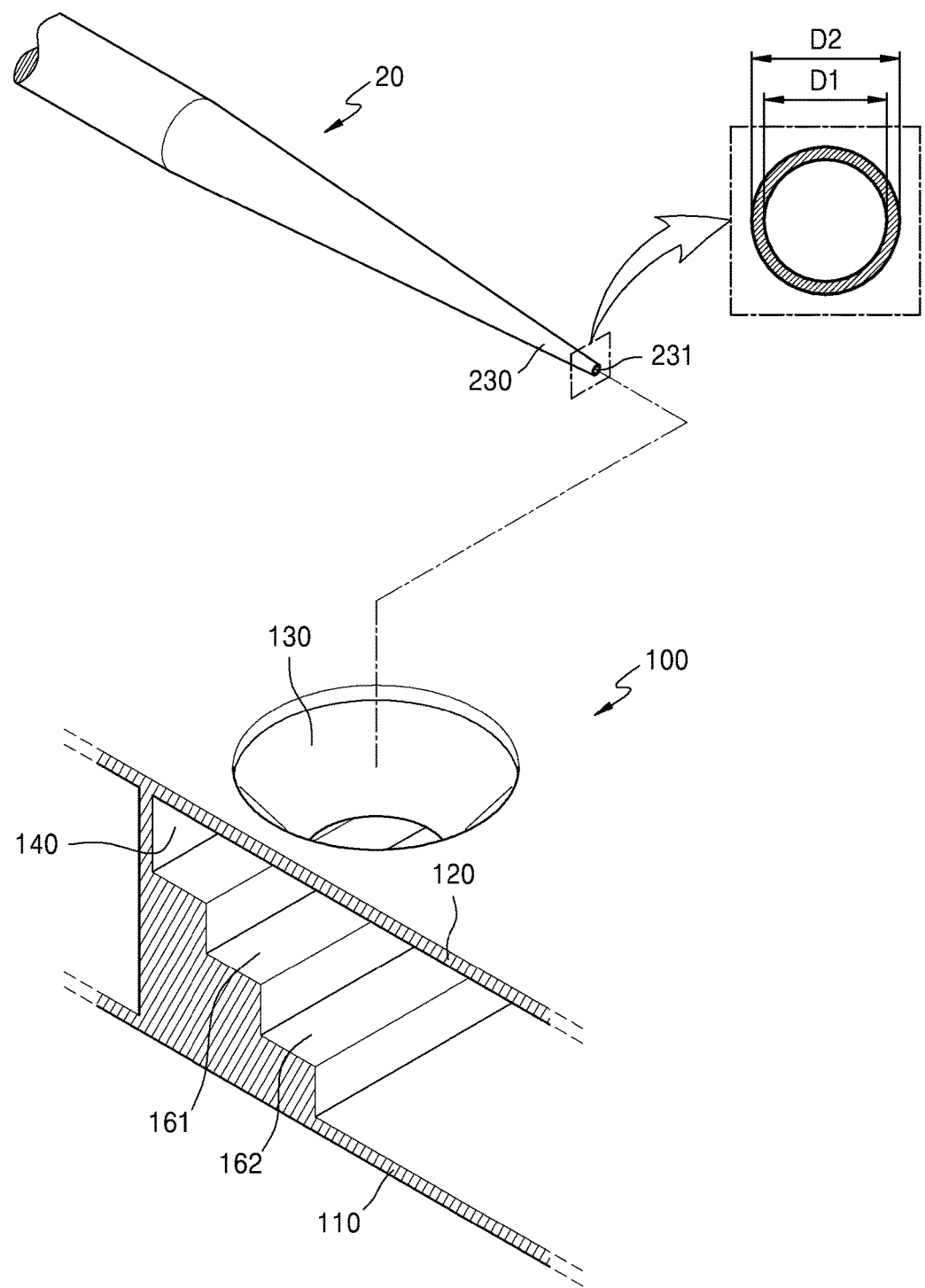
FIG. 2 is a partial perspective view of the specimen inspection apparatus illustrated in FIG. 1 and a specimen transporting apparatus according to an exemplary embodiment.

FIG. 1 is a perspective view of a specimen inspection apparatus 10 according to an exemplary embodiment, and FIG. 2 is a partial perspective view of the specimen inspection apparatus 10 illustrated in FIG. 1 and a specimen transporting apparatus 20 according to an exemplary embodiment.

Referring to FIGS. 1 and 2, the specimen injection apparatus 10 may include a platform 100 having a rotatable disc shape and microfluidic structures that provide a space or a flow path in which a fluid may be accommodated or may flow through the platform 100. The platform 100 may include several plates. Intagliated structures corresponding to chambers or channels may be formed on a surface on which the plates face each other, and the intagliated structures may be bonded to each other, thereby providing a space and a path into the platform 100. Bonding of the plates may be performed using various methods, such as adhesion using an adhesive or a double-sided adhesive tape, ultrasonic fusion, and laser welding. For example, the platform 100 may be a two-plate structure including a lower plate 110 and an upper plate 120, or a structure in which a partitioning plate (not shown) for defining a space in which a fluid may be accommodated between the lower plate 110 and the upper plate 120 and a flow path on which the fluid may flow, is disposed.

Figure 3A:
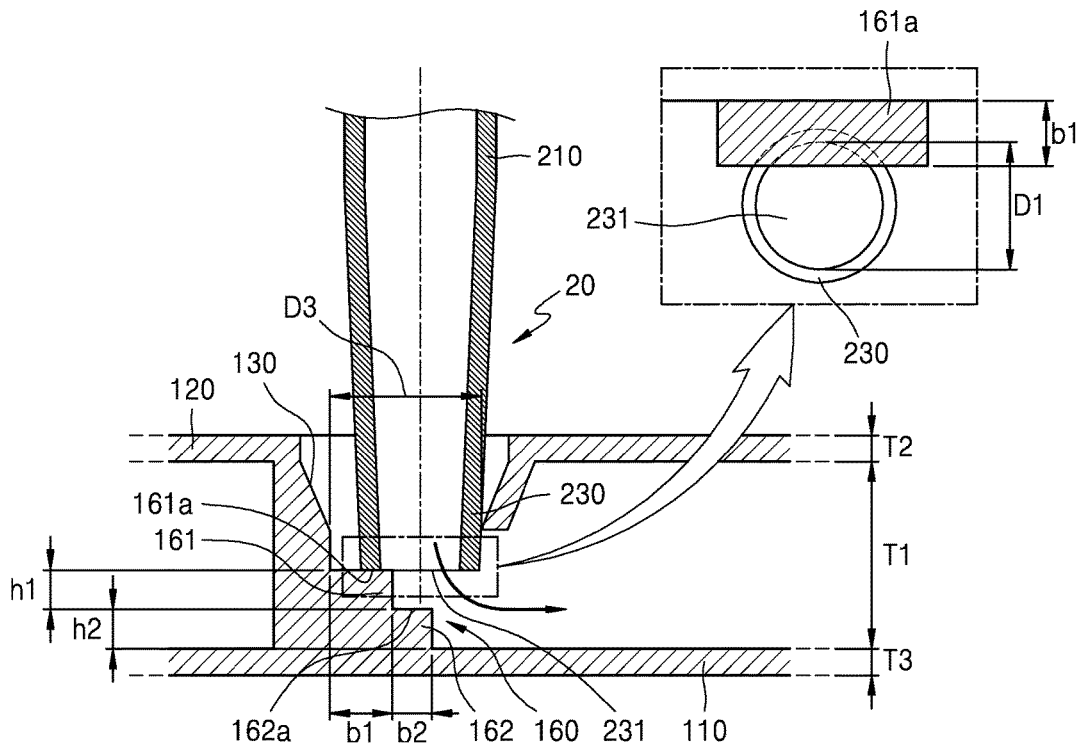
FIGS. 3A and 3B are cross-sectional views illustrating a state in which the specimen transporting apparatus is inserted into an injection part, in the specimen inspection apparatus illustrated in FIG. 2 according to an exemplary embodiment.

A thickness T3 of the lower plate 110 of the platform 100 and a thickness T2 of the upper plate 120 of the platform 100 may differ according to design choice (see FIG. 3A). For example, the thickness T3 of the lower plate 110 of the platform 100 may be about 1 mm to about 10 mm, and the thickness T2 of the upper plate 120 of the platform 100 may be about 0.5 mm to about 3 mm. In the exemplary embodiment, a distance T1 between the lower plate 110 and the upper plate 120 of the platform 100 may be determined according to the thickness T3 of the lower plate 110 of the platform 100 and the thickness T2 of the upper plate 120 of the platform 100. An area close to a center C of the platform 100 in a radial direction of the specimen injection apparatus 10 is referred to as an inner area, and an area distant from the center C of the platform 100 in the radial direction of the specimen injection apparatus 10 is referred to as an outer area. An introduction part 140 may be disposed in an innermost area of the platform 100, and an injection part 130 for injecting a specimen may be disposed in the introduction part 140.

The injection part 130 is an opening through which a front end 230 of the specimen transporting apparatus 20 that will be described later, may be inserted into the injection part 130. For example, the injection part 130 may be formed as a conical-shaped opening. However, exemplary embodiments are not limited thereto.

The specimen transporting apparatus 20 may be a transporting member that is inserted into the injection part 130 and moves the specimen into the specimen inspection apparatus 10 and may include a specimen accommodation part 210 having an axisymmetric cylindrical shape and a front end 230 disposed at one end of the specimen accommodation part 210 along a longitudinal direction of the specimen transporting apparatus 20. The specimen transporting apparatus 20 may be formed to have a conical shape tapering from the specimen accommodation part 210 to the front end 230, and an opening 231, through which the specimen may be injected into or discharged from the injection part 130, may be formed in the front end 230.

The introduction part 140 is a connection path disposed between the injection part 130 and the lower plate 110 of the platform 100. The specimen may flow into the introduction part 140 through the opening 231 of the front end 230 inserted into the injection part 130 and may be accommodated in an inspection part 150 using a channel part 125 that connects the introduction part 140 and the inspection part 150. The inspection part 150 may be an accommodation chamber for accommodating an appropriate amount of specimen suitable for inspection. For example, because a centrifugal force generated by rotation of the platform 100 may be used so as to transport the specimen from the introduction part 140 to the inspection part 150, the inspection part 150 may be placed in an outer area of the specimen injection apparatus 10 than the introduction part 140.

The specimen transporting apparatus 20 may be formed to have various sizes and shapes according to corresponding purposes. For example, when the specimen transporting apparatus 20 is a pipette, a diameter D1 of the opening 231 may be about 0.5 mm to about 1.5 mm, and a diameter D2 of the front end 230 may be about 2.0 mm to about 5 mm. The size and shape of the injection part 130 may be determined to exactly coincide with the size and shape of the front end 230 of the specimen transporting apparatus 20. However, when the size of the injection part 130 is determined in this way, when the specimen is injected, the specimen transporting apparatus 20 may become stuck in the injection part 130 of the specimen inspection apparatus 10, and the specimen inspection apparatus 10 may be contaminated due to backflow of the specimen when the specimen transporting apparatus 20 is not inserted. Also, using the specimen transporting apparatus 20 having the front end 230 of various sizes is not possible in the specimen inspection apparatus 10 having the injection part 130 having a particular size.

In order to prevent the problems discussed above, a diameter D3 (see FIG. 3A) of the injection part 130 may be formed to be larger than the diameter (i.e., an outer diameter) D2 of the front end 230. In the exemplary embodiment, the opening 231 may be clogged according to the position of the front end 230. In order to prevent clogging of the opening 231 that may occur when the diameter D3 of the injection part 130 is formed to be larger than the outer diameter D2 of the front end 230, a structure for supporting the specimen transporting apparatus 20 may be disposed in the introduction part 140 according to an exemplary embodiment. Hereinafter, a support part that may prevent clogging of the opening 231 by supporting the specimen transporting apparatus 20 will be described.

Figure 3B:
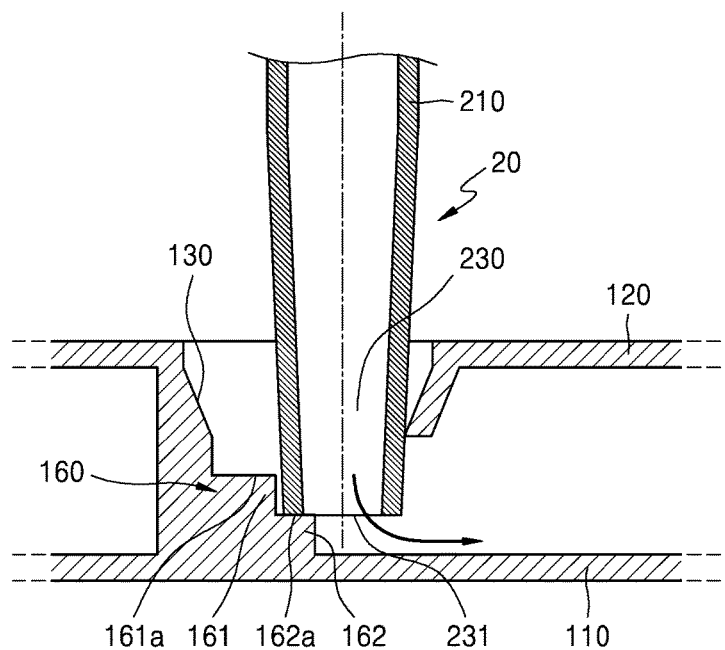

FIGS. 3A and 3B are cross-sectional views showing a state in which the specimen transporting apparatus 20 is inserted into the injection part 130, in the specimen inspection apparatus 10 illustrated in FIG. 2.

As described above, because the diameter D3 of the injection part 130, which is the smallest diameter of the injection part 130, according to an exemplary embodiment may be formed to be larger than the outer diameter D2 of the front end 230, the position of the front end 230 of the specimen transporting apparatus 20 supported by the introduction part 140 may differ. In order to prevent clogging of the opening 231 that may occur when the diameter D3 of the injection part 130 is formed to be larger than the outer diameter D2 of the front end 230, a plurality of stepped parts 160 that is a structure for supporting the specimen transporting apparatus 20 may be disposed in the introduction part 140 according to an exemplary embodiment.

Referring to FIGS. 2, 3A, and 3B, the plurality of stepped parts 160 are supporting members disposed between the injection part 130 and the lower plate 110 of the platform 100. For example, a second stepped part 162 may be disposed on the lower plate 110 of the platform 100, and a second support surface 162a disposed on the second stepped part 162 may be disposed to face the injection part 130. A first stepped part 161 may be disposed on the second support surface 162a, and a first support surface 161a disposed on the first stepped part 161 may be disposed to face the injection part 130.

A first step height h1 of the first stepped part 161 protruding from the second step part 162 and a second step height h2 of the second stepped part 162 protruding from the lower plate 110 may be determined by the distance T1 between the lower plate 110 and the upper plate 120 of the platform 100.

A width b1 of the first support surface 161a and a width b2 of the second support surface 162a may be formed to be smaller than the diameter D1 of the opening 231, for example, to be equal to or less than a half of the diameter D1 of the opening 231. Thus, the specimen accommodated in the specimen accommodation part 210 may be introduced into the introduction part 140 through the opening 231 regardless of the position of the front end 230 inserted into the injection part 130.

For example, as illustrated in FIG. 3A, when the specimen transporting apparatus 20 is inserted into the injection part 130 to face the first support surface 161a along a longitudinal axis, a part of the front end 230 and the opening 231 may be supported by the first support surface 161a. In the exemplary embodiment, the other parts of the front end 230 and the opening 231 may be exposed in the introduction part 140 while not being supported by the first support surface 161a, and the other parts of the opening 231 disposed in the front end 230 may also be exposed in the introduction part 140 while not being supported by the first support surface 161a. Thus, the specimen accommodated in the specimen accommodation part 210 may be introduced into the introduction part 140 through the opening 231 not supported by the first support surface 161a.

As described above, the diameter D3 of the injection part 130 disposed in the specimen inspection apparatus 10 may be formed to be larger than the outer diameter D2 of the front end 230 so that the specimen transporting apparatus 20 having various sizes and shapes may be used in the specimen inspection apparatus 10. Thus, the arrangement of the front end 230 may differ according to a position in which the front end 230 is inserted into the injection part 130.

For example, as illustrated in FIG. 3B, when the specimen transporting apparatus 20 is inserted into the injection part 130 to face the second support surface 162a along the longitudinal axis, a part of the front end 230 and a part of the opening 231 disposed in the front end 230 may be supported by the second support surface 162a. In the exemplary embodiment, the other part of the front end 230 may be exposed in the introduction part 140 while not being supported by the second support surface 162a, and the other part of the opening 231 disposed in the front end 230 may be exposed in the introduction part 140 while not being supported by the second support surface 162a. Thus, the specimen accommodated in the specimen accommodation part 210 may be introduced into the introduction part 140 through the opening 231 exposed in the introduction part 140.

As described above, as the plurality of stepped parts 160 are disposed in the introduction part 140, the specimen accommodated in the specimen accommodation part 210 may be introduced into the introduction part 140 through the opening 231 regardless of the position of the front end 230 inserted into the injection part 130. Thus, the specimen transporting apparatus 20 having the front end 230 with various sizes may be used in the specimen inspection apparatus 10 without clogging of the front end 230 that may occur when the specimen is injected.

Figure 4A:
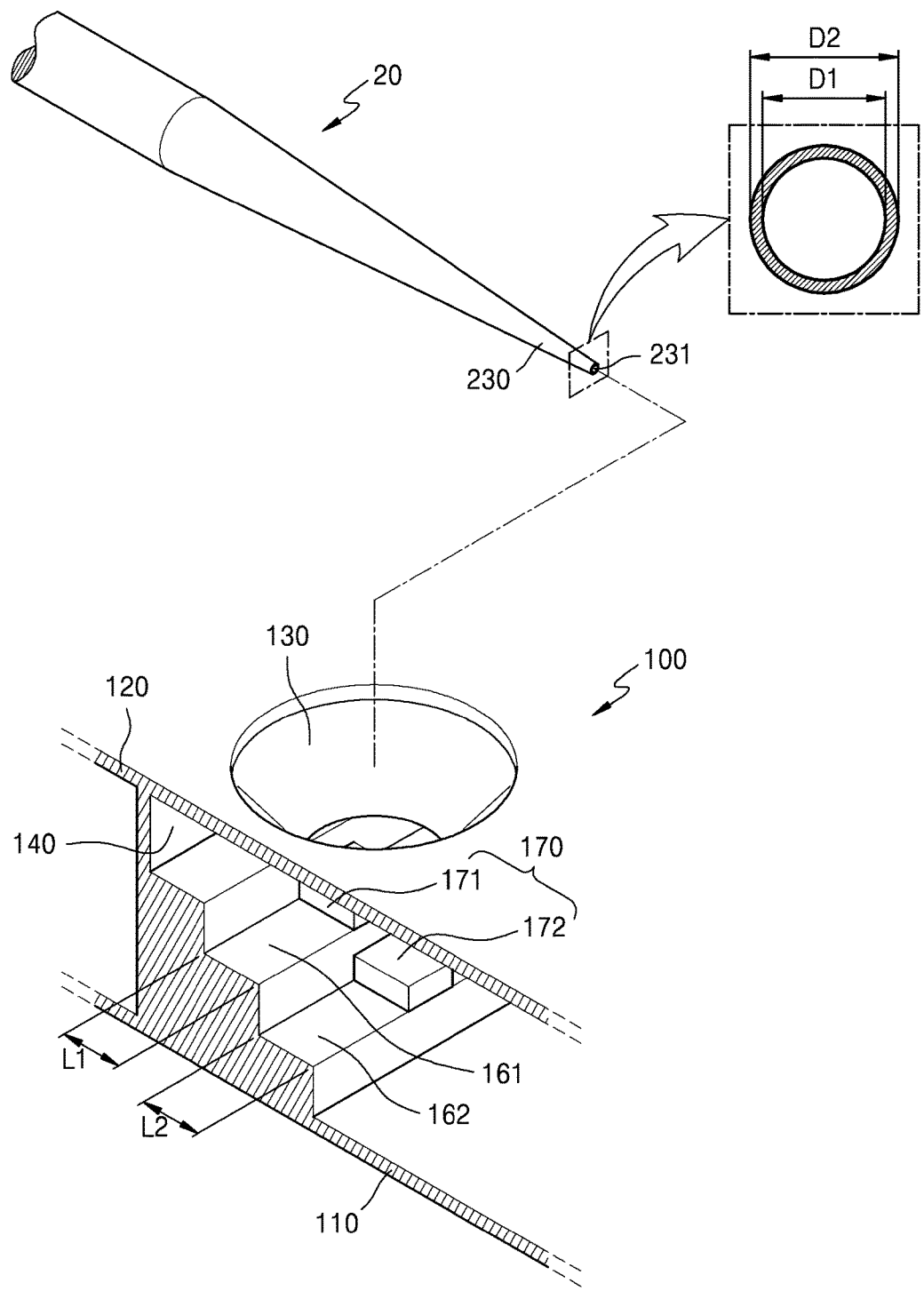
FIG. 4A is a partial perspective view of a specimen inspection apparatus according to an exemplary embodiment.
Figure 4B:
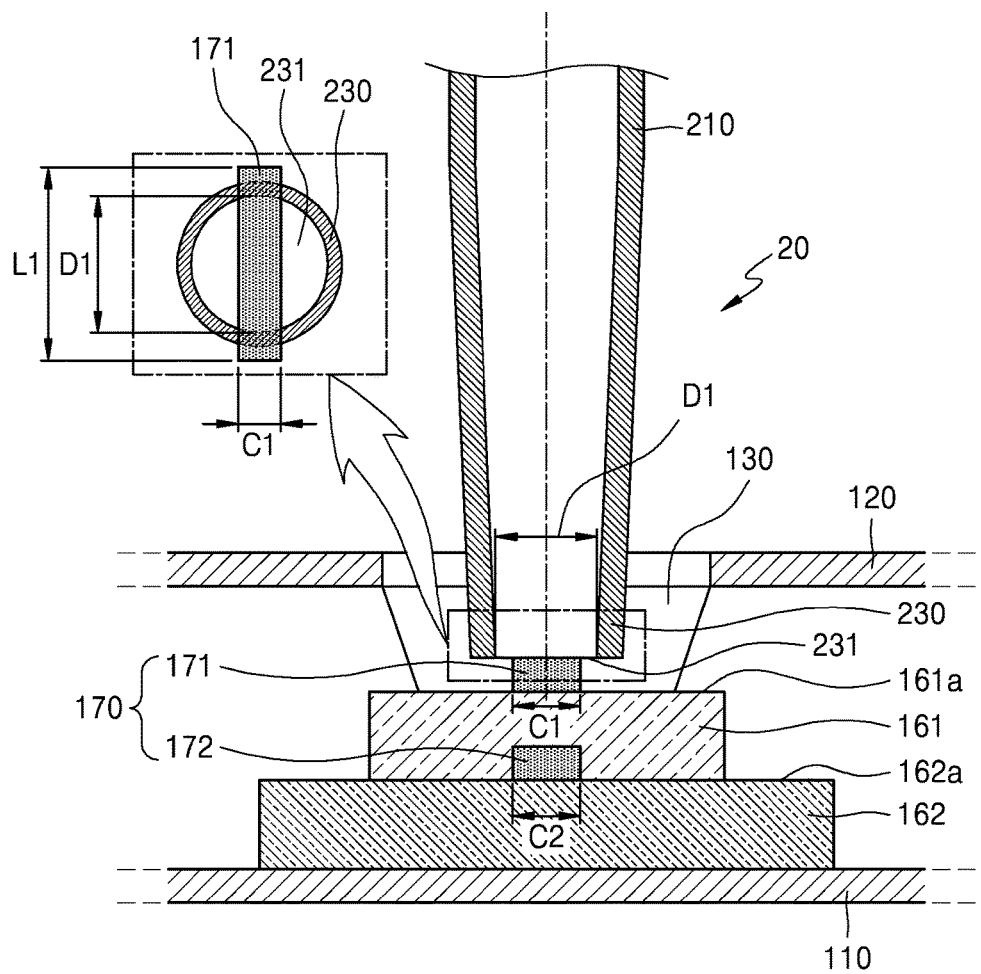
FIG. 4B is a cross-sectional view illustrating a state in which a specimen transporting apparatus is inserted into an injection part, in the specimen inspection apparatus illustrated in FIG. 4A.
Figure 5A:
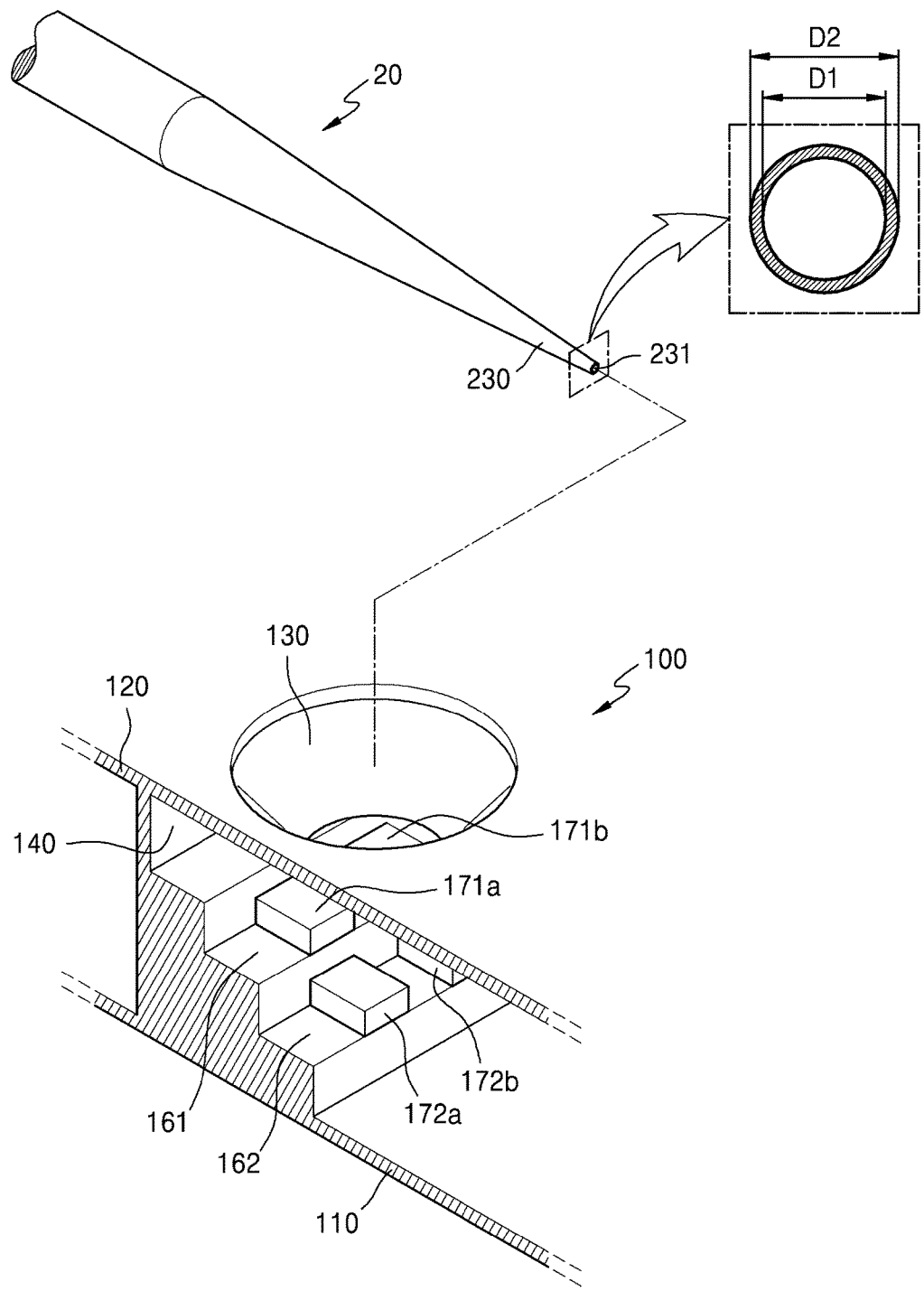
FIG. 5A is a partial perspective view of a specimen inspection apparatus according to an exemplary embodiment.
Figure 5B:
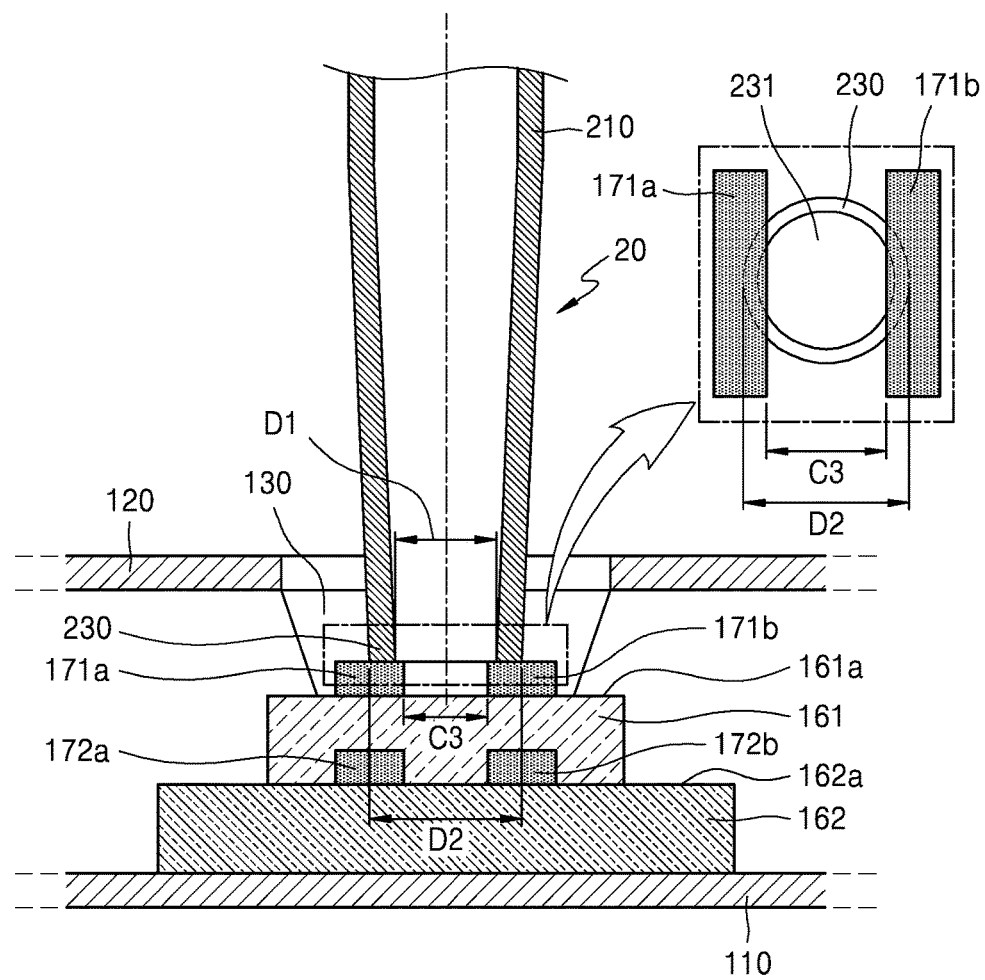
FIG. 5B is a cross-sectional view illustrating a state in which a specimen transporting apparatus is inserted into an injection part, in the specimen inspection apparatus illustrated in FIG. 5A.
Figure 6:
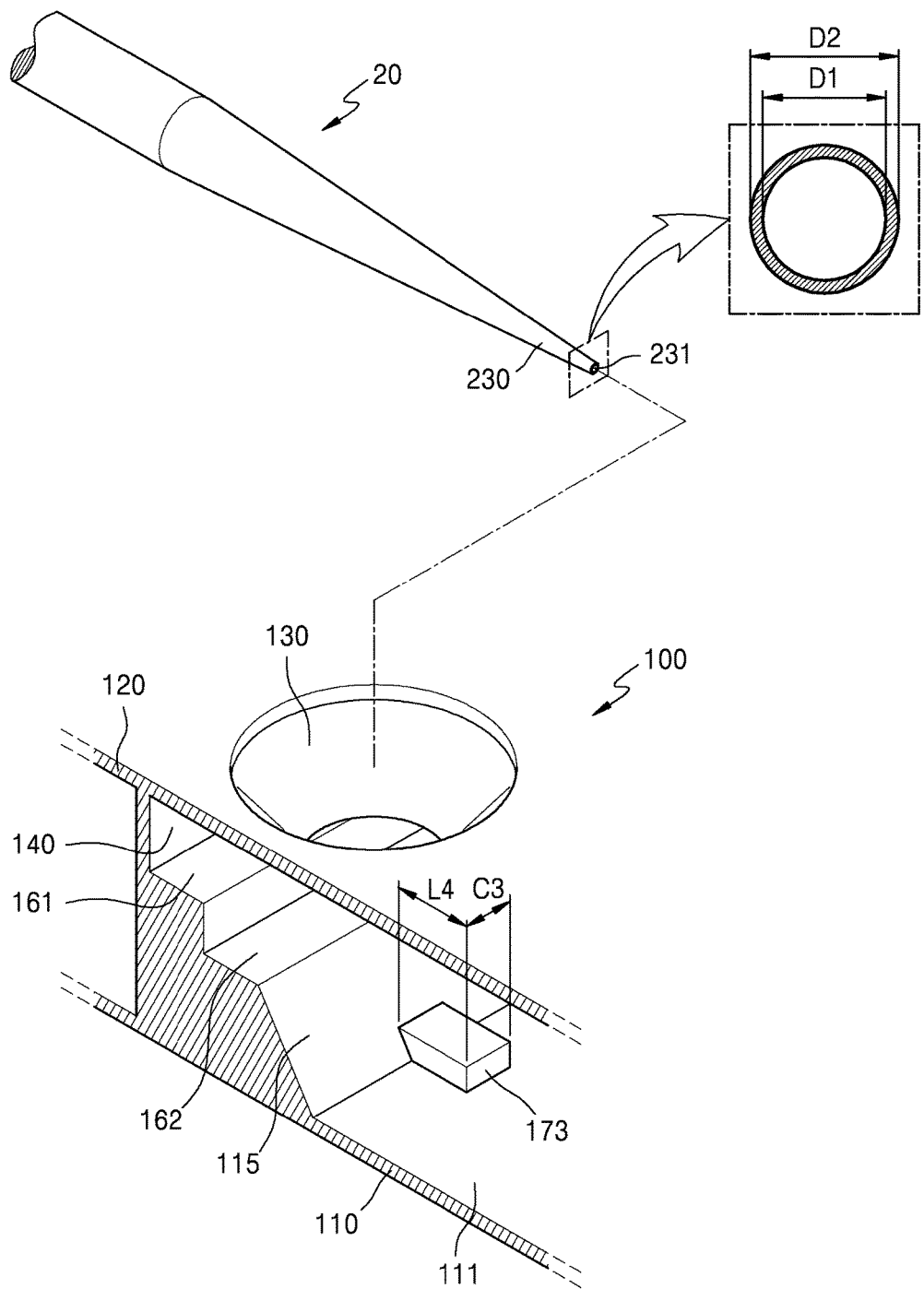
FIG. 6 is a partial perspective view of a specimen inspection apparatus according to an exemplary embodiment.

FIG. 4A is a partial perspective view of a specimen inspection apparatus 10 according to an exemplary embodiment, and FIG. 4B is a cross-sectional view illustrating a state in which a specimen transporting apparatus 20 is inserted into an injection part 130, in the specimen inspection apparatus 10 illustrated in FIG. 4A. FIG. 5A is a partial perspective view of a specimen inspection apparatus 10 according to an exemplary embodiment, and FIG. 5B is a cross-sectional view illustrating a state in which a specimen transporting apparatus 20 is inserted into an injection part 130, in the specimen inspection apparatus 10 illustrated in FIG. 5A, and FIG. 6 is a partial perspective view of a specimen inspection apparatus 10 according to an exemplary embodiment.

As described above, the widths b1 and b2 of the support surfaces 161a and 162a disposed in each of the stepped parts 160 may be formed to be smaller than the inner diameter D1 of the opening 231. However, the specimen transporting apparatus 20 having a more fine diameter D1 (i.e., very small diameter) of the opening 231 may be used according to a use purpose of the specimen transporting apparatus 20. In this case, it may be difficult to form the stepped parts 160 including the support surfaces 161a and 162a having the smaller widths b1 and b2 than the diameter D1 of the opening 231. In the exemplary embodiment, when supporting members having the shape of projection parts 170 are disposed on the support surfaces 161a and 162a of the stepped parts 160, a part of the front end 230 may be supported by the projection parts 170 while the opening 231 is not clogged.

Referring to FIGS. 4A and 4B, a plurality of projection parts 170 may be disposed on the first support surface 161a disposed in each stepped part 160 and may support the part of the front end 230. For example, a first projection part 171 may be disposed on the first support surface 161a disposed in a first stepped part 161, and a second projection part 172 may be disposed on the second support surface 162a disposed in a second stepped part 162. In the exemplary embodiment, each of lengths L1 and L2 of the first and second projection parts 171 and 172 may be formed to be larger than the inner diameter D1 of the opening 231 disposed in the front end 230, and each of widths C1 and C2 of the first and second projection parts 171 and 172 may be formed to be smaller than the diameter D1 of the opening 231 disposed in the front end 230. Thus, in the specimen transporting apparatus 20 having a smaller cross-sectional area than that of the first support surface 161a, the front end 230 inserted into the injection part 130 may be supported by the projection parts 170, and the specimen accommodated in the specimen accommodation part 210 may be introduced into the introduction part 140.

For example, as illustrated in FIG. 4B, when the specimen transporting apparatus 20 is inserted into the injection part 130 to face the first support surface 161a along the longitudinal axis, the part of the front end 230 and the part of the opening 231 disposed in the front end 230 may be supported by the first projection part 171. In the exemplary embodiment, the other part of the front end 230 may be exposed in the introduction part 140 while not being supported by the first projection part 171, and the other part of the opening 231 disposed in the front end 230 may also be exposed in the introduction part 140 while not being supported by the first projection part 171. Thus, the specimen accommodated in the specimen accommodation part 210 may be introduced into the introduction part 140 through the opening 231 exposed to the outside.

In the exemplary embodiment, only one projection part 170 is disposed in the support surface 161a. However, exemplary embodiments are not limited thereto. As illustrated in FIGS. 5A and 5B, a plurality of first projection parts 171a and 171b may be formed on the first support surface 161a. In the exemplary embodiment, the plurality of first projection parts 171a and 171b may be disposed to be spaced apart from each other by a predetermined distance. For example, a predetermined distance C3 formed between the first projection parts 171a and 171b may be formed to be smaller than the inner diameter D2 of the front end 230.

Also, in the exemplary embodiment, a position in which the projection part 170 is formed, is limited to the first support surface 161a disposed in the stepped part 160. However, exemplary embodiments are not limited thereto. For example, the thicknesses T2 and T3 of the lower plate 110 and the upper plate 120 of the platform 100 illustrated in FIG. 3A may be formed to be relatively large. Thus, the distance T1 between the lower plate 110 and the upper plate 120 of the platform 100 for forming the plurality of stepped parts 160 and projection parts 170 may be small. In the exemplary embodiment, when one or more projection parts 170 are disposed not on the first and second support surfaces 161a and 162a of the stepped part 160 but on a bottom part 111 of the lower plate 110, one or more projection parts 170 may be disposed in the introduction part 140 despite the distance T1 between the lower plate 110 and the upper plate 120 of the platform 100 being relatively small.

For example, referring to FIG. 6, a third projection part 173 may be formed on the bottom part 111 of the lower plate 110. In this case, a length L4 of the third projection part 173 may be formed to be larger than the diameter D1 of the opening 231, and a width C4 of a fourth projection part 174 may be formed to be smaller than the diameter D1 of the opening 231 disposed in the front end 230. Also, an inclined side part 115 may be formed between the lower plate 110 of the platform 100 and the stepped part 160 so as to form a predetermined angle between the side part 115 and the bottom part 111 of the lower plate 110, and the third projection part 173 may be disposed to face the center of the injection part 130. Thus, when a user inserts the front end 230 of the specimen transporting apparatus 20 into the injection part 130, the front end 230 may be moved in an axial direction along the side part 115. Thus, the part of the front end 230 may be supported by the third projection part 173 disposed in the center of the injection part 130. Thus, because the user may support the part of the front end 230 on the third projection part 173 regardless of a position in which the front end 230 is inserted into the injection part 130, even when the distance T3 between the upper plate 120 and the lower plate 110 of the platform 100 is relatively small, the specimen transporting apparatus 20 may be easily mounted on the specimen inspection apparatus 10.

Figure 7A:
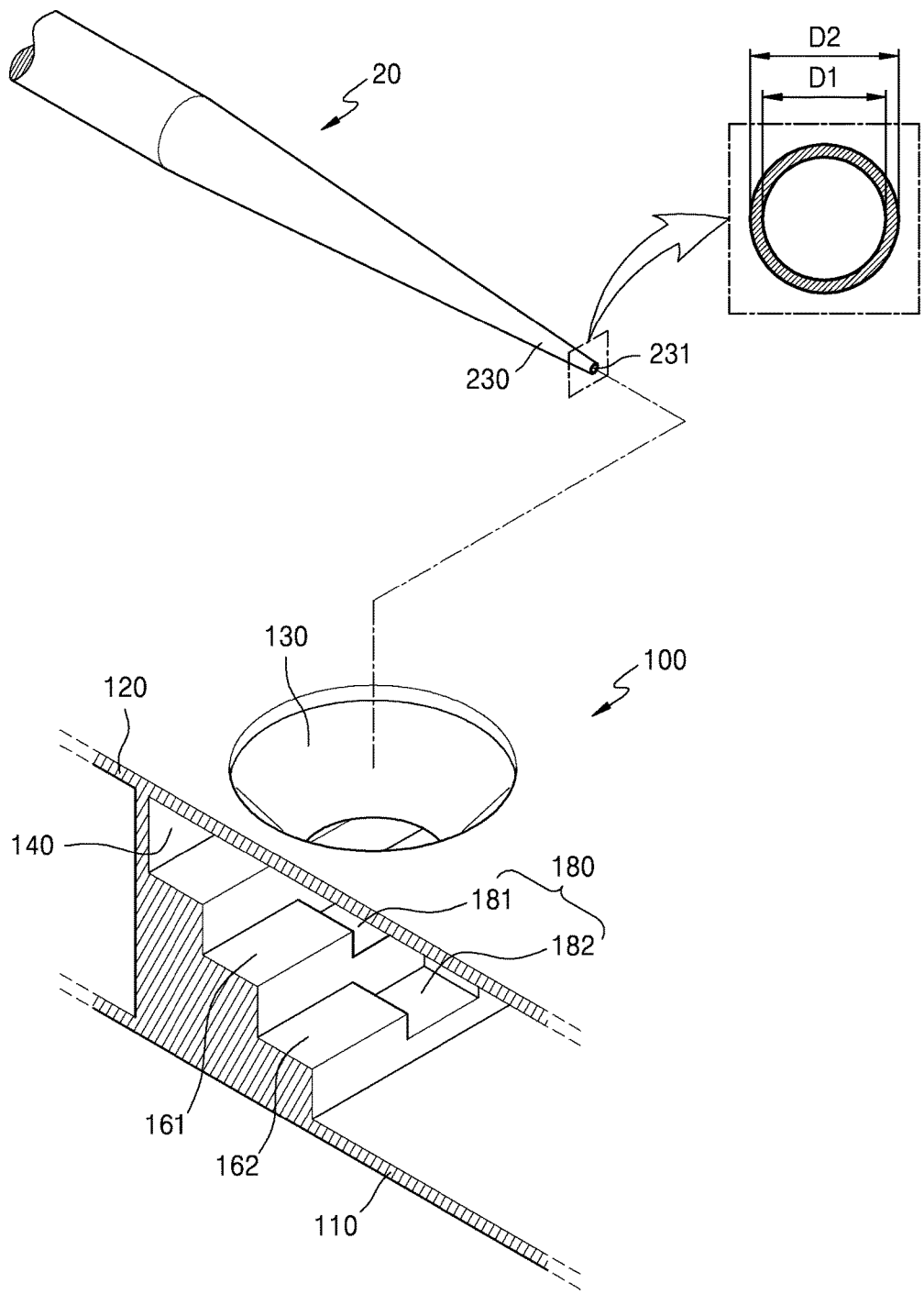
FIG. 7A is a partial perspective view of a specimen inspection apparatus according to an exemplary embodiment.
Figure 7B:
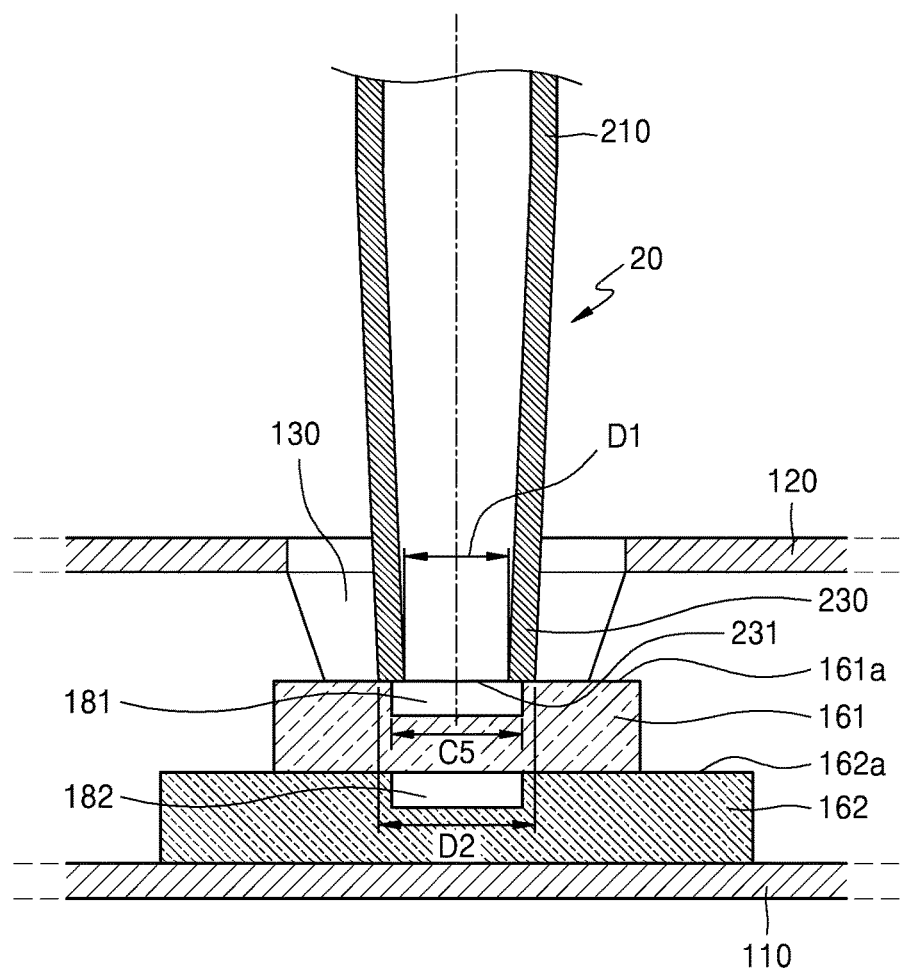
FIG. 7B is a cross-sectional view illustrating a state in which a specimen transporting apparatus is inserted into an injection part, in the specimen inspection apparatus illustrated in FIG. 7A.
Figure 8A:
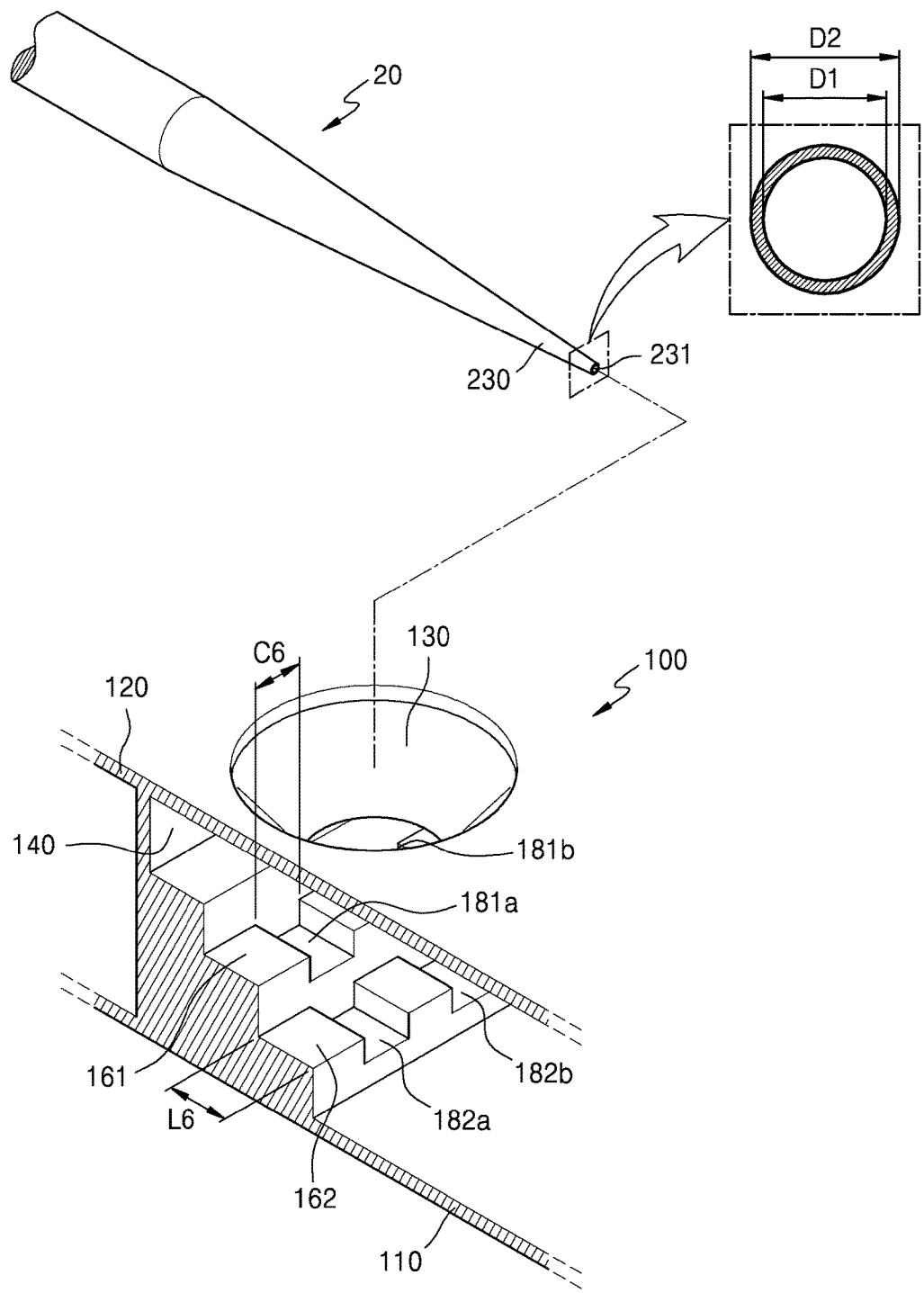
FIG. 8A is a partial perspective view of a specimen inspection apparatus according to an exemplary embodiment.
Figure 8B:
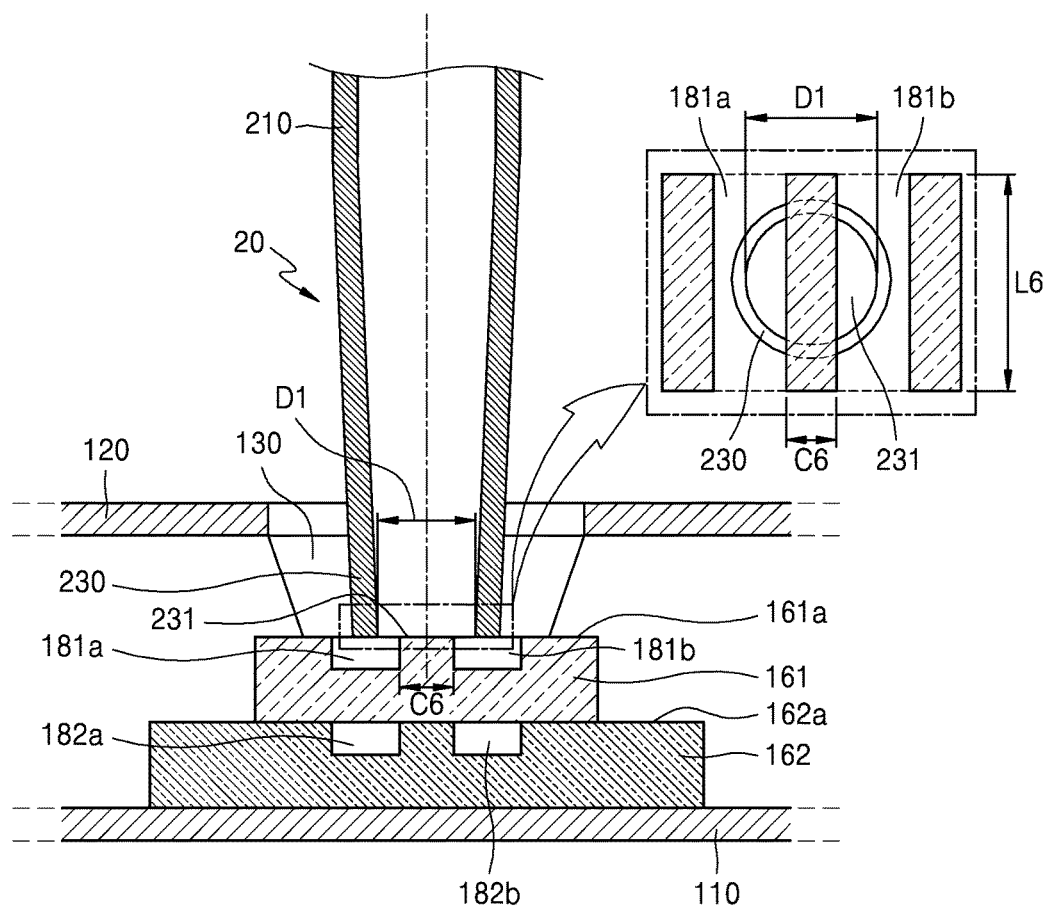
FIG. 8B is a cross-sectional view illustrating a state in which a specimen transporting apparatus is inserted into an injection part, in the specimen inspection apparatus illustrated in FIG. 8A.
Figure 9:
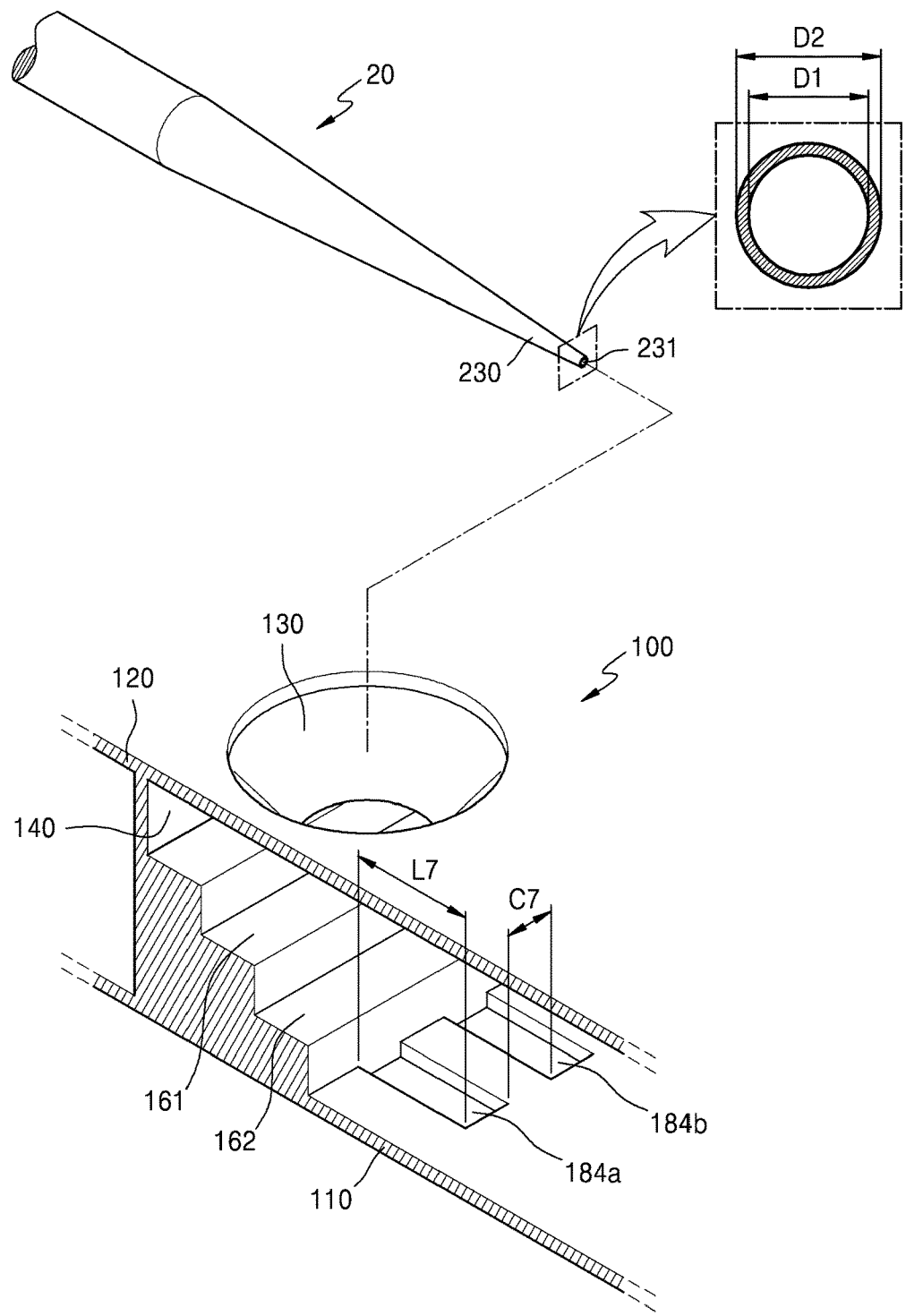
FIG. 9 is a partial perspective view of a specimen inspection apparatus according to an exemplary embodiment.

FIG. 7A is a partial perspective view of a specimen inspection apparatus 10 according to an exemplary embodiment, and FIG. 7B is a cross-sectional view illustrating a state in which a specimen transporting apparatus 20 is inserted into an injection part 130, in the specimen inspection apparatus 10 illustrated in FIG. 7A. FIG. 8A is a partial perspective view of a specimen inspection apparatus 10 according to an exemplary embodiment, and FIG. 8B is a cross-sectional view illustrating a state in which a specimen transporting apparatus 20 is inserted into an injection part 130, in the specimen inspection apparatus illustrated in FIG. 8A. FIG. 9 is a partial perspective view of a specimen inspection apparatus 10 according to an exemplary embodiment.

Referring to FIG. 3A, it may be difficult to form the above-described projection parts 170 on the first and second support surfaces 161a and 162a of the stepped part 160 of the specimen inspection apparatus 10 having the small distance T1 between the lower plate 110 and the upper plate 120 of the platform 100. In particular, when the thicknesses T2 and T3 of the lower plate 110 and the upper plate 120 of the platform 100 are large, the distance T1 between the lower plate 110 and the upper plate 120 of the platform 100 may be relatively small. Thus, no space in which the plurality of projection parts 170 are formed, may be formed.

According to an exemplary embodiment, when the distance T1 between the lower plate 110 and the upper plate 120 of the platform 100 is relatively small, groove parts 180 may be formed in the first and second support surfaces 161a and 162a of the stepped part 160 disposed in the specimen inspection apparatus 10. Thus, the part of the front end 230 may be supported by the groove parts 180 while the opening 231 is not clogged.

Referring to FIGS. 7A and 7B, a plurality of groove parts 180 may be disposed in the first support surface 161a of the stepped part 160 and may support the part of the front end 230. For example, a first groove part 181 may be disposed on the first support surface 161a disposed in the first stepped part 161, and a second groove part 182 may be disposed on the second support surface 162a disposed in the second stepped part 162. In the exemplary embodiment, a width C5 of the first and second groove parts 181 and 182 may be formed to be smaller than the width of the front end 230, for example, the diameter D2 of the front end 230. Thus, in the specimen transporting apparatus 20 having the diameter D1 of the opening 231 that is relatively small, the front end 230 may be supported by the groove part 180, and the specimen accommodated in the specimen accommodation part 210 may be introduced into the introduction part 140.

For example, as illustrated in FIG. 7B, when the specimen transporting apparatus 20 is inserted into the injection part 130 to face the first support surface 161a, only the part of the front end 230 may be supported by the first support surface 161a, and the opening 231 may be exposed to the outside by the first groove part 181. Thus, the specimen accommodated in the specimen accommodation part 210 may be introduced into the introduction part 140 through the opening 231 exposed to the outside.

In the exemplary embodiment, only one groove part 180 is disposed in the first support surface 161a. However, exemplary embodiments are not limited thereto. As illustrated in FIGS. 8A and 8B, the plurality of first parts 181a and 181b may be formed in the first support surface 161a, and the plurality of second support parts 182a and 182b may be formed in the second support surface 162a. In the exemplary embodiment, the plurality of first groove parts 181a and 181b and the plurality of second parts 182a and 182b may be disposed to be spaced apart from each other by a predetermined distance C6 and may be formed to have a predetermined width L6. For example, the width L6 of the first groove parts 181a and 181b and the second groove parts 182a and 182b may be formed to be larger than the diameter D1 of the opening 231. The predetermined distance C6 formed between the first groove parts 181a and 181b and the second groove parts 182a and 182b may be formed to be smaller than the width of the opening 231, for example, the diameter D1 of the opening 231.

Also, in the exemplary embodiment, positions in which the groove parts 180 are formed, are limited to the first and second support surfaces 161a and 162a disposed in the stepped part 160. However, exemplary embodiments are not limited thereto. When the distance T1 between the lower plate 110 and the upper plate 120 of the platform 100 is small to form the plurality of stepped parts 160, one or more fourth groove parts 184 may be disposed in the bottom part 111 of the lower plate 110. For example, as illustrated in FIG. 9, the plurality of first groove parts 184a and 184b may be formed in the bottom part 111 of the lower plate 110. In the exemplary embodiment, the plurality of fourth groove parts 184a and 184b may be formed to have a predetermined width L7 and may be disposed to be spaced apart from each other by the predetermined distance C7. In the exemplary embodiment, the predetermined width L7 of the fourth groove parts 184a and 184b and the predetermined distance C7 formed between the fourth groove parts 184a and 184b may be formed to be smaller than the diameter D1 of the opening 231, as described above.

As described above, a specimen transporting apparatus having a front end of various sizes may be used in a specimen inspection apparatus according to the one or more of the exemplary embodiments. Clogging of the front end that may occur when a specimen is injected, may be prevented, or the specimen transporting apparatus may be prevented from becoming stuck in the specimen inspection apparatus, and contamination of the specimen inspection apparatus due to backflow of the specimen when the specimen transporting apparatus is not inserted may be prevented.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While exemplary embodiments have been particularly shown and described above, it will be understood by those of ordinary skill in the art that various changes in form and details may be made therein without departing from the spirit and scope as defined by the following claims.

What is claimed is:

1. A specimen inspection apparatus into which a specimen transporting apparatus is inserted, the specimen inspection apparatus comprising:
   a platform comprising an upper plate and a lower plate disposed to face each other and to be spaced apart from each other by a predetermined distance;
   an injection part provided in the upper plate, the injection part being configured to receive a front end of the specimen transporting apparatus;
   an introduction part connected to the injection part and provided between a bottom surface of the upper plate and a top surface of the lower plate;
   a plurality of stepped parts provided in the introduction part; and
   a projection part provided on the lower plate and facing the injection part,
   wherein the plurality of stepped parts has a descending staircase shape and comprises a first step part including a first support surface and a second step part including a second support surface, and the second support surface is lower in a vertical direction than the first support surface,
   wherein the plurality of stepped parts are arranged in a linear direction, and
   wherein a length of the projection part is larger than a diameter of an opening disposed in the front end, and a width of the projection part is smaller than the diameter of the opening disposed in the front end.

2. The specimen inspection apparatus of claim 1, wherein another diameter of the injection part is larger than the diameter of the opening disposed in the front end of the specimen transporting apparatus.

3. The specimen inspection apparatus of claim 1, wherein:
   the front end comprises the opening through which specimen is injected into or ejected out of the specimen transporting apparatus;
   the first and second support surfaces are disposed to face the injection part; and
   a width of each of the first and second support surfaces is smaller than the diameter of the opening disposed in the front end of the specimen transporting apparatus.

4. The specimen inspection apparatus of claim 3, wherein the width of each of the first and second step parts is less than or equal to a half of the diameter of the opening.

5. The specimen inspection apparatus of claim 1, further comprising a side part forming a non-perpendicular predetermined angle with the lower plate and provided between the plurality of stepped parts and the lower plate.

6. The specimen inspection apparatus of claim 1, wherein the projection part comprises a plurality of projection parts, the plurality of projection parts provided on the lower plate and spaced apart from one another by a distance that is smaller than the diameter of the opening disposed in the front end.

7. The specimen inspection apparatus of claim 1, wherein the specimen transporting apparatus is a pipette.

8. A specimen inspection apparatus into which a specimen transporting apparatus is inserted, the specimen inspection apparatus comprising:
   a platform comprising an upper plate and a lower plate disposed to face each other and to be spaced apart from each other by a predetermined distance;

an injection part provided in the upper plate, a front end of the specimen transporting apparatus being inserted into the injection part;

an introduction part connected to the injection part and provided between the upper plate and the lower plate; and a plurality of stepped parts provided in the introduction part;

wherein the plurality of stepped parts comprises a first step part including a first support surface and a second step part including a second support surface, the first and second support surfaces disposed to face the injection part, wherein the plurality of stepped parts further comprises a projection part provided on each of the first and second support surfaces and facing the injection part.

9. The specimen inspection apparatus of claim 8, wherein a length of the projection part is larger than a diameter of an opening disposed in the front end, and a width of the projection part is smaller than the diameter of the opening disposed in the front end.

10. The specimen inspection apparatus of claim 8, wherein the projection part comprises a plurality of projection parts, the plurality of projection parts provided on each of the first and second support surfaces and provided to be spaced apart from one another by a distance that is smaller than a diameter of the front end.

11. A specimen inspection apparatus into which a specimen transporting apparatus is inserted, the specimen inspection apparatus comprising:

a platform comprising an upper plate and a lower plate disposed to face each other and to be spaced apart from each other by a predetermined distance;

an injection part provided in the upper plate, a front end of the specimen transporting apparatus being inserted into the injection part;

an introduction part connected to the injection part and provided between the upper plate and the lower plate; and a plurality of stepped parts provided in the introduction part;

wherein the plurality of stepped parts comprises a first step part including a first support surface and a second step part including a second support surface, the first and second support surfaces disposed to face the injection part, wherein the plurality of stepped parts further comprises a groove part provided in each of the first and second support surfaces and facing the injection part.

12. The specimen inspection apparatus of claim 11, wherein a width of the groove part is smaller than a diameter of the front end of the specimen transporting apparatus.

13. The specimen inspection apparatus of claim 11, wherein:

the groove part comprises a plurality of groove parts, the plurality of groove parts are provided on each of the first and second support surfaces and provided to be spaced apart from one another by a second predetermined distance; and a length of each groove part is larger than a diameter of an opening disposed in the front end, and the second distance is smaller than the diameter of the opening disposed in the front end.

14. A specimen inspection apparatus into which a specimen transporting apparatus is inserted, the specimen inspection apparatus comprising:

a platform comprising an upper plate and a lower plate disposed to face each other and to be spaced apart from each other by a predetermined distance;

an injection part provided in the upper plate, the injection part being configured to receive a front end of the specimen transporting apparatus;

an introduction part connected to the injection part and provided between a bottom surface of the upper plate and a top surface of the lower plate;

a plurality of stepped parts provided in the introduction part; and a groove part provided in the lower plate and facing the injection part, wherein the plurality of stepped parts has a descending staircase shape and comprises a first step part including a first support surface and a second step part including a second support surface, and the second support surface is lower in a vertical direction than the first support surface, wherein the plurality of stepped parts are arranged in a linear direction, and wherein a width of the groove part is smaller than a diameter of the front end of the specimen transporting apparatus.

15. The specimen inspection apparatus of claim 14, wherein:

the groove part comprises a plurality of groove parts, the plurality of groove parts provided in the lower plate and spaced apart from one another by a second predetermined distance; and the front end comprises an opening through which specimen is injected into or ejected out of the specimen transporting apparatus, a length of each groove part being larger than the another diameter of the opening disposed in the front end, and the second predetermined distance being smaller than the other diameter of the opening disposed in the front end.

* * * * *